US010301589B2

(12) United States Patent
Al Harethi et al.

(10) Patent No.: US 10,301,589 B2
(45) Date of Patent: May 28, 2019

(54) HIGH SALINITY TOLERANT MICROALGAE STRAINS, PRODUCTS DERIVED THEREFORM, AND METHODS OF PRODUCING THE SAME

(71) Applicant: Khalifa University of Science and Technology, Abu Dhabi (AE)

(72) Inventors: Ahmed Husain Al Harethi, Abu Dhabi (AE); Hector Hugo Hernandez, Abu Dhabi (AE)

(73) Assignee: Khalifa University of Science and Technology (AE)

( * ) Notice: Subject to any disclaimer, the term of this patent is extended or adjusted under 35 U.S.C. 154(b) by 0 days.

(21) Appl. No.: 15/268,867

(22) Filed: Sep. 19, 2016

(65) Prior Publication Data

US 2017/0096633 A1 Apr. 6, 2017

Related U.S. Application Data

(63) Continuation of application No. 14/057,099, filed on Oct. 18, 2013, now abandoned.

(60) Provisional application No. 61/723,053, filed on Nov. 6, 2012, provisional application No. 61/716,225, filed on Oct. 19, 2012.

(51) Int. Cl.
*C12N 1/12* (2006.01)
*C12N 1/36* (2006.01)
*C12P 7/64* (2006.01)

(52) U.S. Cl.
CPC .............. *C12N 1/12* (2013.01); *C12N 1/36* (2013.01); *C12P 7/6409* (2013.01); *C12P 7/649* (2013.01); *Y02E 50/13* (2013.01)

(58) Field of Classification Search
None
See application file for complete search history.

(56) References Cited

U.S. PATENT DOCUMENTS

| 5,711,983 | A  | 1/1998  | Kyle et al. |
| 8,187,453 | B2 | 5/2012  | Kale |
| 8,222,010 | B2 | 7/2012  | Franklin et al. |
| 8,278,090 | B1 | 10/2012 | Im et al. |

OTHER PUBLICATIONS

Mishra, et al.., 2008. Physiological characterization and stress induced metabolic responses of Dunaliella salina isolated from salt pan. J. Ind. Microbial. BiotechnoL 35, 1093-1101.*
Batterton et al., Arch. Mikrobiol. 76, 151-165 (1971).*
Hemlata et al., Screening of Cyanobacteria for Phycobiliproteins and Effect of Different Environmental Stress on its Yield. Bulletin of Environmental Contamination and Toxicology, 2009. 83(4): 509-515.*
Liu et al., Hypersalinity Enhances the Production of Extracellular Polymeric Substance (EPS) in the Texas Brown Tide Alga, *Aureoumbra lagunensis* (Pelagophyceae). Journal of Phycology, 2000. 36: 71-77.*
Mishra et al., Isolation and Characterization of Extracellular Polymeric Substances from Micro-Algae *Dunaliella salina* Under Salt Stress. Bioresource Technology, 2009. 100: 3382-3386.*
Tonk et al., Aquatic Microbial Ecology. 46: 117-123, 2007.*
Takagi et al. Journal of Bioscience and Bioengineering, 2006, vol. 101, No. 3, 223-226.*
Ferroni et al., American Journal of Botany 94(12): 1972-1983. 2007.*
Anders S. Carlsson et al., *Micro- and Macro-Algae: Utility for Industrial Applications*. Outputs from the EPOBIO Project, Sep. 2007.
Brennan, L. and P. Owende, *Biofuels from Micro-Algae—A Review of Technologies for Production, Processing, and Extractions of Biofuels and Co-products*. Renewable and Sustainable Energy Reviews, 2010. 14(2): p. 557-577.
Borowitzka, M.A., *Commercial Production of Microalgae: Ponds, Tanks, Tubes and Fermenters*. Journal of Biotechnology, 1999. 70(1-3): p. 313-321.
Chisti, Y., *Biodiesel from Microalgae*. Biotechnology Advances, 2007. 25(3): p. 294-306.
Christaki, E. et al., *Functional Properties of Carotenoids Originating from Algae*. Journal of the Science of Food and Agriculture, 2013. 93: 5-11.
Delgado-Vargas, F. et al., *Natural Pigments: Carotenoids, Anthocyanins, and Betalains-Characteristics, Biosynthesis, Processing, and Stability*. Critical Reviews in Food Science and Nutrition, 2000. 40(3): p. 173-289.
Ferrell, J. et al., *National Algal Biofuels Technology Roadmap: A Technology Roadmap Resulting from the National Algal Biofuels Workship*Dec. 9-10, 2008, College Park, Maryland, 2010. Washington, DC: U.S. Department of Energy, Office of Energy Efficiency and Renewable Energy, Biomass Program.
Ghasemi, Y. et al., *Microalgae Biofuel Potentials*. Applied Biochemistry and Microbiology, 2012. 48(2): p. 150-168.
Hagerthey, S.E. et al., *Evaluation of Pigment Extraction Methods and a Recommended Protocol for Periphyton Chlorophyll-a Determination and Chemotaxonomic Assesment*. Journal of Phycology, 2006. 42: 1125-1136.
Hejazi, M.A. et al., *Selective Extraction of Carotenoids from the Microalga Dunaliella salina with Retention of Viability*, Biotechnology and Bioengineering, 2002. 79: 29-36.
Hamlata et al., *Screening of Cyanobacteria for Phycobiliproteins and Effect of Different Environmental Stress on its Yield*. Bulletin of Environmental Contamination and Toxicology, 2009, 83(4):509-515.
James, S.C. et al., *Modeling Algae Growth in an Open-Channel Raceway*. Journal of Computational Biology, 2010, 17(7): p. 895-906.
Kerr, R.A., *The Story of O2*. Science, 2005. 308(5729): p. 1730-1732.

(Continued)

*Primary Examiner* — Irene Marx
(74) *Attorney, Agent, or Firm* — Hayes Soloway PC

(57) ABSTRACT

The present invention relates generally to microalgae strains that are tolerant to high salinity, the products derived from the high salinity tolerant microalgae strains, and methods of producing high salinity tolerant microalgae strains and their products.

9 Claims, 11 Drawing Sheets

(56) References Cited

OTHER PUBLICATIONS

Khan, S.A. et al., *Prospects of Biodiesel Production from Microalgae in India*. Renewable and Sustainable Energy Reviews, 2009. 13: 2361-2372.
Lancelot, C. et al., *Modeling Phytoplankton Blooms and Carbon Export Production in the Southern Ocean: Dominant Controls by Light and Iron in the Atlantic Sector in Austral Spring 1992*. Deep Sea Research Part 1, 2000. 47:1621-1662.
Larkum, A.W.D. et al., *Selection, Breeding and Engineering of Microalgae for Bioenergy and Biofuel Production*. Trends in Biotechnology, 2012. 30(4): 198-205.
Liu, H. and Buskhey, E.J., *Hypersalinity Enhances the Production of Extracellular Polymeric Substance (EPS) in the Texas Brown Tide Alga, Aureoumbra lagunensis(Pelagophyceae)*. Journal of Phycology, 2000. 36: 71-77.
Mata, T.M., et al., *Microalgae for Biodiesel Production and Other Applications; A Review*. Renewable and Sustainable Energy Reviews, 2010, 14: 217-232.
Mishra, A. and Jha, B., *Isolation and Characterization of Extracellular Polymeric Substances from Micro-Algae Dunaliella salina Under Salt Stress*. Bioresource Technology, 2009. 100: 3382-3386.
Mutanda, T. et al., *Bioprospecting for Hyper-Lipid Producing Microalgal Strains for Sustainable Biofuel Production*. Bioresource Technoiogy, 2011. 102: 57-70.
Ogawa, T. et al., *Effect of Oxygen on the Growth (Yield) of Chlorella Vulgaris*. Archives of Microbiology, 1980. 127(1): p. 25-31.
Ourisson, G. et al., *The Microbial Origin of Fossil Fuels*. Scientific American, 1984, 251(2): p. 44-51.
Ozturk, S. and Aslim, B., *Modification of Exopolysaccharide Composition and Production by Three Cyanobacterial Isolates Under Salt Stress*. Environmental Science and Pollution Research, 2010. 17: 595-602.
Prieto, A. et al., *Assessment of Carotenoid Production by Dunaliella Salina in Different Culture Systems and Operation Regimes*. Journal of Biotechnology, 2011. 151(2): 180-185.
Rodriguez, J. et al., *An Implementation Framework for Wastewater Treatment Models Requiring a Minimum Programming Expertise*. Water Science & Technology, 2009. 59(2): p. 367-380.
Sarkar, C.R. et al., *A Comparative Study of Carotenoid Extraction from Algae in Different Solvent Systems*. Asian Journal of Plant Science and Research, 2012. 2: 546-549.
Singh, J. and Gu, S., *Commercialization Potential of Microalgae for Biofuels Production*. Renewable and Sustainable Energy Reviews, 2010 14(9): p. 2596-2610.
Spolaore, P. et al., *Commercial Applications of Microalgae*. Journal of Bioscience and Bioengineering, 2006. 101(2): p. 87-96.
Takaichi, S., *Carotenoids in Algae: Distributions, Biosyntheses and Functions*. Marine Drugs, 2011. 9: 1101-1118.
Tran, H. et al., *Statistical Optimization of Culture Media for Growth and Lipid Production of Botryococcus Braunii* LB572, Biotechnology and Bioprocess Engineering, 2010. 15: 277-284.
Ugwu, C.U. et al., *Light/Dark Cyclic Movement of Algal Culture (Synechocystis aquatilis) Outdoor Inclined Tubular Photobioreactor Equipped with Static Mixers for Efficient Production of Biomass*. Biotechnology Letters, 2005. 27: 75-78.
Bonen, Linda and Doolittle, W. Ford, "On the Prokaryotic Nature of Red Algal Chloroplasts", *Proc. Nat. Acad. Sci. USA*, 72(6):2310-2314 (1975).
Fox, G.E. et al., "The Phylogeny of Prokaryotes", American Association for the Advancement of Science, 209(4455):457-463 (1980).
Hickman, Michael, "Blue-green Algae", *The Canadian Encyclopedia*, Published Feb. 6, 2016, 3 pages.

* cited by examiner

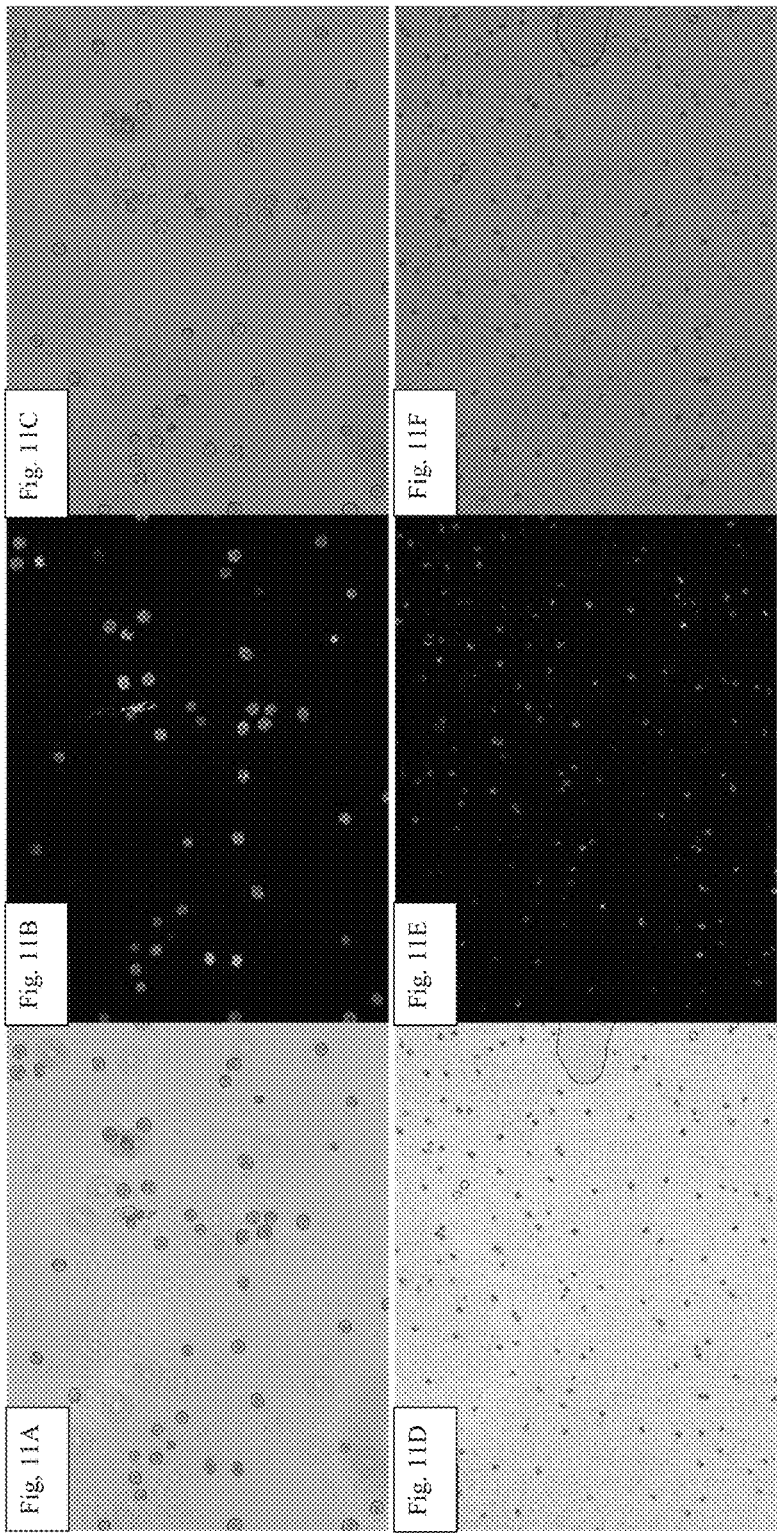

HIGH SALINITY TOLERANT MICROALGAE STRAINS, PRODUCTS DERIVED THEREFORM, AND METHODS OF PRODUCING THE SAME

RELATED APPLICATIONS

This application claims the benefit of and priority from U.S. Provisional Application Ser. No. 61/716,225, filed on Oct. 19, 2012, and 61/723,053, filed on Nov. 6, 2012, the disclosure of each of which is hereby incorporated herein by reference in its entirety.

FIELD OF THE INVENTION

The present invention relates generally to microalgae strains that are tolerant to high salinity, the products derived from the high salinity tolerant microalgae strains, and methods of producing high salinity tolerant microalgae strains and their products.

SUMMARY OF THE INVENTION

A first aspect of the present invention comprises a method of producing a high salinity tolerant microalgae strain comprising: subjecting a microalgae cell to serially increased concentrations of a salt sufficient to produce the high salinity tolerant microalgae strain.

A second aspect of the present invention comprises a microalgae strain produced by a method of the present invention.

A further aspect of the present invention comprises a method of growing a high salinity tolerant microalgae strain comprising growing the high salinity tolerant microalgae strain in a medium comprising a high salinity.

Another aspect of the present invention comprises a method of producing a secondary metabolite comprising: growing a microalgae cell in a medium having a salinity in a range from about 25 parts per thousand (ppt) to about 70 ppt and in an environment having a carbon dioxide concentration at about atmospheric levels, thereby producing the secondary metabolite.

A further aspect of the present invention comprises a microalgae having a buoyancy that changes with salinity.

Another aspect of the present invention comprises a microalgae that grows in a medium having a salinity in a range from about 50 ppt to about 400 ppt.

An additional aspect of the present invention comprises a microalgae that transforms morphology and/or modifies excreted extracellular polymeric substances in response to changes in salinity.

Another aspect of the present invention comprises a new and distinct strain of algae plant having the characteristics described and illustrated herein.

A further aspect of the present invention comprises an isolated high salinity tolerant microalgae strain having the characteristics described and illustrated herein.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

BRIEF DESCRIPTION OF THE DRAWINGS

FIGS. 8A and 8B show the optical density profiles from an ascending temperature experiment, where growth media at two salinities (33 ppt and 100 ppt) were used in PSI-FMT-150 to cultivate an algae strain in chemostat mode at 0.175 ml/min growth media and sparging compressed air. FIG. 8C shows the pH profile from an ascending temperature experiment, where growth media at two salinities (33 ppt and 100 ppt) were used in PSI-FMT-150 to cultivate an algae strain in chemostat mode at 0.175 ml/min growth media and sparging compressed air.

FIGS. 11A-11F show fluorescent microscopy images of the isolated wild type strain and the AAH001 strain at 460× magnification. FIG. 11A shows a bright field image of the wild type algae strain isolate grown under 33 ppt salinity. FIG. 11B shows a green fluorescent image of the wild type strain grown at 33 ppt salinity. FIG. 11C shows a composite image of the wild type strain grown under 33 ppt salinity. FIG. 11D shows a bright field image of the AAH001 strain grown at 300 ppt salinity. FIG. 11E shows a green fluorescent image of photosynthetic centers of the AAH001 strain grown at 300 ppt salinity. FIG. 11F shows a composite image of the AAH001 strain grown at 300 ppt salinity.

DETAILED DESCRIPTION OF THE INVENTION

Figure 1:
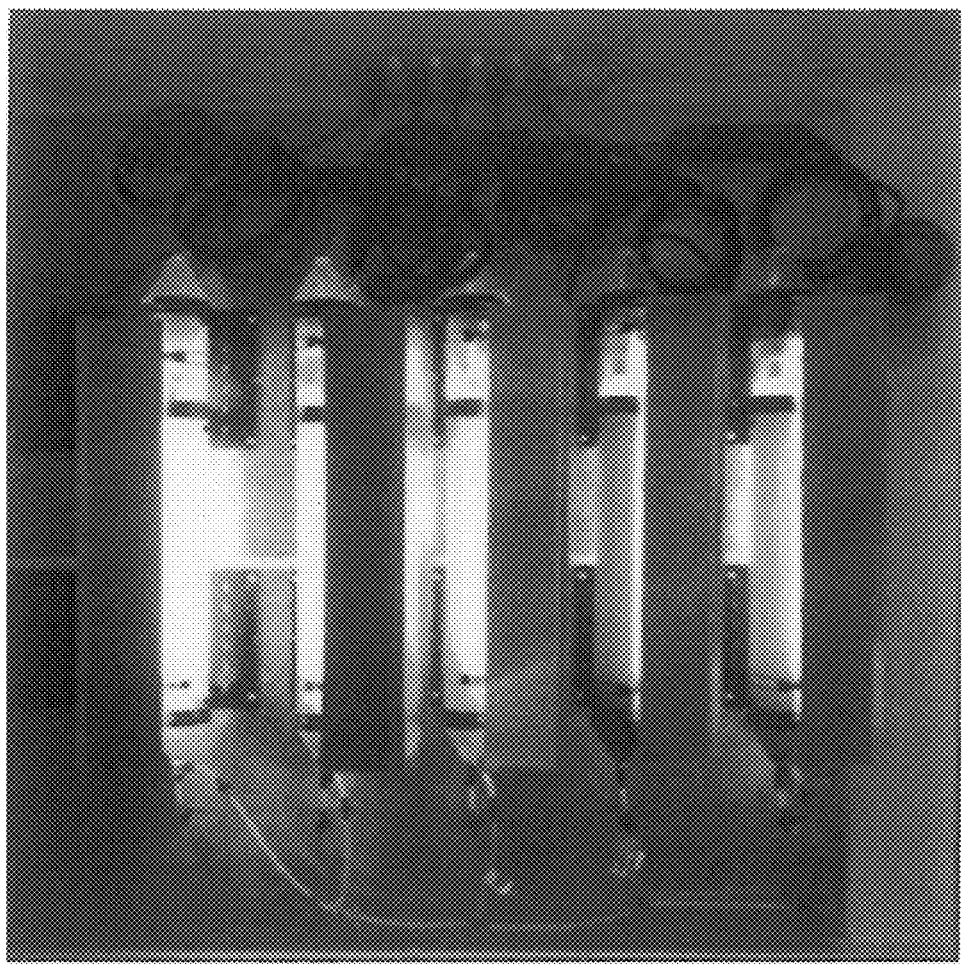
FIG. 1 shows the cultivation of an isolated microalgae strain at five different salinities on a 16/8 light/dark cycle.

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz*, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration (e.g., salinity) and the like, is meant to encompass variations of ±20%, ±10%, ±5%, ±1%, ±0.5%, or even ±0.1% of the specified amount.

The present invention provides a high salinity tolerant microalgae strain. The terms "strain" and "variety" are used interchangeably herein and refer to a genetic variant of a species of algae. "High salinity tolerant microalgae strain" as used herein refers to a microalgae strain that is able to grow in a medium comprising a high salinity. The medium may be a natural medium (e.g., ocean water) and/or an artificial medium (e.g., artificial seawater) that may optionally be supplemented with one or more nutrients. Exemplary nutrients include, but are not limited to, nitrogen such as potassium nitrate, phosphorus such as potassium phosphate, silicon, metals such as copper and iron, micronutrients, and any combination thereof. In some embodiments of the present invention, the medium is synthetic seawater.

"Grow", "growth", "growing", and grammatical variants thereof of as used herein refer to an increase in biomass of the microalgae. As those skilled in the field will recognize, the terms "grow", "growth", "growing", and grammatical variants thereof of as used herein describe that the microalgae cell is continuing to proceed through its growth phases and to reproduce. Microalgae growth may be measured by methods known to those of skill in the art. In some embodiments of the present invention, microalgae growth may be determined by measuring the growth rate of the microalgae (i.e., by measuring the increase or decrease in biomass over time).

"High salinity" as used herein refers to a salt content of at least about 50 parts per thousand (ppt) or more. In some embodiments of the present invention, high salinity refers to a salt content in a range from about 50 ppt to about 400 ppt, or any range and/or individual value therein. Exemplary salinity ranges include, but are not limited to, from about 100 ppt to about 400 ppt, about 200 ppt to about 300 ppt, or about 300 ppt to about 400 ppt. In certain embodiments of the present invention, high salinity refers to a salinity of at least about 100 ppt, about 125 ppt, about 150 ppt, about 175 ppt, about 200 ppt, about 225 ppt, about 250 ppt, about 275 ppt, about 300 ppt, about 325 ppt, about 350 ppt, about 375 ppt, or about 400 ppt.

According to some embodiments of the present invention, a high salinity tolerant microalgae strain of the present invention grows in a medium having a salinity in a range from about 0 ppt to about 400 ppt, or any range and/or individual value therein. Exemplary ranges include, but are not limited to, from about 10 ppt to about 400 ppt, about 30 ppt to about 400 ppt, about 50 ppt to about 400 ppt, about 75 ppt to about 400 ppt, about 100 ppt to about 400 ppt, about 150 ppt to about 400 ppt, about 200 ppt to about 300 ppt, about 250 ppt to about 350 ppt, about 200 ppt to about 400 ppt, about 250 ppt to about 400 ppt, or about 300 ppt to about 400 ppt. In certain embodiments of the present invention, a high salinity tolerant microalgae strain of the present invention grows in a medium having a salinity of about 0 ppt, about 30 ppt, about 50 ppt, about 75 ppt, about 100 ppt, about 125 ppt, about 150 ppt, about 175 ppt, about 200 ppt, about 225 ppt, about 250 ppt, about 275 ppt, about 300 ppt, about 325 ppt, about 350 ppt, about 375 ppt, or about 400 ppt.

A high salinity tolerant microalgae strain of the present invention may be isolated. "Isolated" and grammatical variants thereof, as used herein refer to an algae existing apart from its native environment. An isolated algae may exist in a purified form that is at least partially separated from at least some of the other components of the naturally occurring algae. In certain embodiments of the present invention, an isolated high salinity tolerant microalgae strain of the present invention may be a wild microalgae. In some embodiments of the present invention, an isolated high salinity tolerant microalgae strain of the present invention may be a wild microalgae that is native to the United Arab Emirates. In other embodiments of the present invention, an isolated high salinity tolerant microalgae strain of the present invention may be a microalgae strain that is distinct from a wild microalgae strain.

According to some embodiments of the present invention, an isolated high salinity tolerant microalgae strain may be provided that can grow and/or be cultivated in a medium having a salinity of greater than 150 ppt, such as, but not limited to, 155 ppt, 160 ppt, 170 ppt, or greater. In certain embodiments of the present invention, an isolated high salinity tolerant microalgae strain may be provided that can grow and/or be cultivated in a medium having a salinity of greater than 250 ppt, such as, but not limited to, 255 ppt, 260 ppt, 275 ppt, 290 ppt, or greater.

An isolated high salinity tolerant microalgae of the present invention can be cultivated and/or grown in a medium comprising a high salinity, such as, but not limited to a salinity greater than 150 ppt, and the microalgae can have a growth of two or more (e.g., 3, 4, 5, etc.) orders of magnitude over the growth period and/or an increase in optical density over time. This can be determined by endpoint visual cell counting, such as, but not limited to, by using microscopy and/or hemocytometer.

In some embodiments of the present invention, a high salinity tolerant microalgae strain of the present invention has a buoyancy that changes with salinity. In certain embodiments of the present invention, a high salinity tolerant microalgae strain of the present invention has a buoyancy that decreases as salinity increases. In some embodiments of the present invention, the settling of a high salinity tolerant microalgae strain of the present invention increases until the salinity reaches about 100 ppt and at about 125 ppt the settling behavior changes and the microalgae settles in stratified layers.

A high salinity tolerant microalgae of the present invention may have an increased tolerance to salinity compared to a wild algae, such as, but not limited to, a wild algae of the same species as the high salinity tolerant microalgae strain. In some embodiments of the present invention, increased tolerance may be measured by the highest salinity a high salinity tolerant microalgae of the present invention is able to grow in compared to the highest salinity a wild algae is able to grow in. In certain embodiments of the present invention, a high salinity tolerant microalgae of the present invention is able to grow in a medium having a salinity that is at least about 5% greater than the salinity of a medium a wild algae is able to grow in. Thus, for example, the high salinity tolerant microalgae of the present invention may have an increased tolerance of about 5%, 10%, 15%, 20%, 25%, 30%, 35%, 40%, . . . 100%, 200%, or more, or any range and/or individual value therein, as compared to a wild algae. In some embodiments of the present invention, a high salinity tolerant microalgae of the present invention has a growth rate that is greater than a wild type microalgae of the same species when grown under the same conditions (e.g., same medium, temperature, etc.). In certain embodiments of the present invention, a high salinity tolerant microalgae of the present invention has a growth rate that is greater than a wild type microalgae of the same species when grown under the same conditions in a medium having a high salinity.

A high salinity tolerant microalgae of the present invention may be any suitable microalgae. Exemplary microalgae include, but are not limited to, microalgae that is in a phylum of Chlorophyta, Charophyta, Rhodophyta, Phaeophyta, Myzozoa, Haptophyta, Ochrophyta, Glaucophyta, Chlorarachniophyte, Heterokont, Cryptomonad, Dinoflagellate, or Euglenid and the like. In some embodiments of the present invention, a high salinity tolerant microalgae strain of the present invention is a member of Chlorophyta. Further exemplary microalgae include, but are not limited to, *Botryococcus braunii*, *Chlorella* sp., *Crypthecodinium cohnnii*, *Cylindrotheca* sp., *Dunaliella primolecta*, *Isochrysis* sp., *Monallantus salina*, *Nannochloris* sp., *Nannochloropsis* sp., *Neochloris oleoabundans*, *Nitzschia* sp., *Phaeodactylum tricornutum*, *Schizochytrium* sp., *Tetraselmis sueica*, those described in U.S. Pat. Nos. 8,278,090, 8,222,010, 8,187,463, and 5,711,983 the contents of each of which are incorporated herein by reference in their entirety, and the like.

In particular embodiments of the present invention, a high salinity tolerant microalgae strain of the present invention may be a green algae, a red algae, a diatom, and any combination thereof. In certain embodiments of the present invention, a high salinity tolerant microalgae strain of the present invention is a green algae. Exemplary green microalgae include, but are not limited to, green microalgae from the family of Dunaliellaceae, Characiochloridaceae, Chlamydomonadaceae, Golenkiniaceae, Spondylomoraceae, Tetrabaenaceae, Volvocaceae, Haematococcaceae, Asteromonadaceae, Astrephomenaceae, Phacotaceae, Oocystaceae, Chlorellaceae, Eremosphaeraceae, Characiosiphonaceae, and the like.

A high salinity tolerant microalgae strain of the present invention may produce a secondary metabolite. Exemplary secondary metabolites include, but are not limited to, alkaloids, aromatic compounds, alcohols, macrolides, peptides, terpenes, carotenoids, toxins volatile organic compounds, peptides, lipopolysaccharides, lipids, hydrocarbons, oils, antioxidants, fatty acids, enzymes, polymers, and any combination thereof. In some embodiments of the present invention, a high salinity tolerant microalgae strain of the present invention may produce a secondary metabolite that is and/or may be used in preparing a carbon-based nutritional, a nutraceutical, a pharmaceutical, a chemical feedstock, a biofuel, a cosmetic, and any combination thereof.

In some embodiments of the present invention, a high salinity tolerant microalgae strain of the present invention may have a fatty acid content of greater than about 20% when grown under environmental $CO_2$ conditions, such as, but not limited to, about 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, or more and/or any range therein.

In certain embodiments of the present invention, a high salinity tolerant microalgae strain of the present invention may excrete a secondary metabolite. In some embodiments of the present invention, a high salinity tolerant microalgae strain of the present invention may produce and/or excrete a secondary metabolite having an absorbance maxima at about 230 nm and about 271 nm with a broad shoulder at about 430 nm. A high salinity tolerant microalgae strain of the present invention may produce and/or excrete a secondary metabolite that is red and/or orange in color when present in and/or excreted into an aqueous medium.

A high salinity tolerant microalgae strain of the present invention may express a secondary metabolite in measurable quantities in about 1 hour to about 4 days, or any range and/or individual value therein. In some embodiments of the present invention, a high salinity tolerant microalgae strain of the present invention may express a secondary metabolite in measurable quantities within about 24 hours to about 36 hours.

In some embodiments of the present invention, a high salinity tolerant microalgae of the present invention transforms morphology and/or modifies excreted extracellular polymeric substances in response to changes in salinity. In certain embodiments of the present invention, when contacted with a medium having a salinity of about 100 ppt or more, the cell of a high salinity tolerant microalgae of the present invention changes morphology and/or an extracellular polymeric substance appears. The extracellular polymeric substances may comprise peptides, polypeptides, proteins, lipids, polysaccharides, nucleic acids, and any combination thereof. The extracellular polymeric substances may form any shape, such as, for example, tubular, circular, etc., and the shape may be uniform or nonuniform. In some embodiments of the present invention, a high salinity tolerant microalgae of the present invention has an oil content from about 10% to about 90% by dry weight, or any range and/or individual value therein.

In some embodiments of the present invention, a high salinity tolerant microalgae of the present invention may grow at a temperature greater than about 5° C. In certain embodiments of the present invention, a high salinity tolerant microalgae of the present invention may grow at a temperature in a range from about 5° C. to about 60° C., or any range and/or individual value therein, such as, but not limited to, from about 10° C. to about 40° C., about 20° C. to about 60° C., about 35° C. to about 60° C., about 15° C. to about 35° C., or about 20° C. to about 30° C. In some embodiments of the present invention, non-arable land may be used to grow a high salinity tolerant microalgae of the present invention. In some embodiments of the present invention, a high salinity tolerant microalgae of the present invention may grow in non-potable sources of water, such as, but not limited to, brackish groundwater, wastewater, and/or seawater.

Another aspect of the present invention comprises a method of producing a high salinity tolerant microalgae strain of the present invention. A method of the present invention may comprise a directed evolution of a microalgae to produce a high salinity tolerant microalgae of the present invention. A directed evolution of a microalgae may comprise subjecting a microalgae (e.g., a microalgae cell) to serially increased concentrations of a salt, thereby producing a high salinity tolerant microalgae strain as compared to a microalgae (e.g., a microalgae cell) not subjected to serially increased concentrations of a salt. In some embodiments, the serially increased concentrations of a salt may increase by the same amount and/or a different amount as compared to another increase in the series. For example, the salt concentration may serially increase by about 5 ppt, 10 ppt, 20 ppt, 25 ppt, 30 ppt, 40 ppt, 50 ppt, 75 ppt, or more at each increase in the series.

According to some embodiments of the present invention, a method of producing a high salinity tolerant microalgae strain of the present invention may comprise subjecting a microalgae (e.g., a microalgae cell) to serially increased concentrations of a salt, thereby producing the high salinity tolerant microalgae strain as compared to a microalgae (e.g., a microalgae cell) not subjected to serially increased concentrations of a salt. A microalgae (e.g., a microalgae cell) used in a method of the present invention may be any suitable microalgae, such as, but not limited to, those described herein. The subjecting step may comprise contacting, growing, culturing and/or the like the microalgae with and/or in a medium whose salinity is serially increased. In some embodiments of the present invention, the subjecting step comprises growing a microalgae in a medium under conditions comprising serially increasing the salinity of the medium, thereby producing a high salinity tolerant microalgae strain of the present invention as compared to a microalgae not grown under conditions comprising serially increasing the salinity of the medium. The subjecting step may comprise two or more additions of a salt, such as, but not limited to, 2, 3, 4, 5, 6, 7, 8, 9, 10, or more salt additions. Each salt addition may increase the salinity of the medium by the same amount and/or a different amount as compared to another salt addition. The salt concentration may increase by about 100 ppt or less, such as, but not limited to, 50 ppt or 25 ppt, compared to the salt concentration prior to the increase. In some embodiments of the present invention, the subjecting step may comprise cyclically repeating one or more salt additions.

The salt used in a method of the present invention may be any suitable salt in any suitable form (e.g., solid, aqueous solution, etc.). Exemplary salts include, but are not limited to, sodium chloride, sodium sulfate, magnesium chloride, magnesium sulfate, calcium chloride, calcium sulfate, sodium bicarbonate, potassium chloride, potassium sulfate, potassium carbonate, a carbonic acid, and any combination thereof. In some embodiments of the present invention, the salt is sodium chloride. In certain embodiments of the present invention, a salt may comprise a salt found in natural sea and/or ocean water.

"Serially increasing", "serially increased", and grammatical variants thereof as used herein refer to a series of salt additions. The series of salt additions may comprise incrementally increasing the salinity of a medium in which a microalgae is grown and/or a medium to be added to a microalgae to two or more salinity levels, such as, but not limited to 2, 3, 4, 5, 6, 7, 8, 9, 10 or more different salinity levels. In some embodiments of the present invention, serially increasing comprises directly adding a salt to a medium in which a microalgae is being grown and/or cultured. In other embodiments of the present invention, serially increasing comprises adding a salt to a medium, such as, but not limited to a culture medium, and subjecting the medium to a microalgae to increase the salinity the microalgae is exposed to. In certain embodiments of the present invention, serially increasing comprises removing or passaging all or a portion of the microalgae (e.g., about 1%, 5%, 10%, . . . 50%, 75%, or more) from a medium of lower salinity to a medium of higher salinity. Thus, the microalgae are passaged stepwise into higher salinity growth media.

The series of salt additions may provide a salinity in a range from about 30 ppt to about 400 ppt, or any range and/or individual value therein, wherein each salt addition in the series of salt additions provides an increase in salinity. Each salt addition in the series of salt additions may provide the same and/or a different amount of increase in salinity as another salt addition. In some embodiments of the present invention, the series of salt additions may provide a salinity in a range from about 30 ppt to about 300 ppt, about 50 ppt to about 400 ppt, or about 30 ppt to about 350 ppt. The series of salt additions may comprise two or more separate salt additions, such as, but not limited to, 2, 3, 4, 5, 6, 7, 8, 9, 10 or more separate salt additions. In certain embodiments of the present invention, serially increasing comprises at least two separate salt additions comprising increasing the salinity of a medium to a salinity in a range from about 50 ppt to about 100 ppt and to a salinity in a range from about 100 ppt to about 400 ppt. The series of salt additions may be carried out over a period of time of about 1 day to about 20 days or more, or any range and/or individual value therein. In some embodiments of the present invention the series of salt additions may be carried out over a period of time of about 1, 2, 3, 4, 5, 6, 7, 8, 9, 10, 11, 12, 13, 14, 15, 16, 17, 18, 19, 20, 21, 22, 23, 24 days or more. In certain embodiments of the present invention the series of salt additions may be carried out over about 14 days.

Each salt addition in a series of salt additions may be separated from the immediately preceding salt addition by about 30 minutes or more, or any range and/or individual value therein, such as, but not limited to, about 1, 2, 3, 4, 5, 6, 7, 8, 9, 10, 11, 12, 13, 14, 15, 16, 17, 18, 19, 20, 21, 22, 23 hours or about 1, 2, 3, 4, 5, 6, 7, 8, 9, 10, 11, 12, 13, 14, 15, 16, 17, 18, 19, 20 days or more, or any range therein. In some embodiments of the present invention, each salt addition is separated from the immediately preceding salt addition by about 6 hours to about 24 hours or about 14 days. In some embodiments of the present invention, this may allow for the microalgae to adjust to the increase in salinity. In some embodiments of the present invention, each salt addition in a series of salt additions is separated from the immediately preceding salt addition by the amount of time sufficient for a microalgae to reach mid- to late-log phase growth. As those skilled in the field will recognize, this time will be dependent on the microalgal species being grown and the growth conditions provided. Thus, the amount of time separating two consecutive salt additions may be the same and/or different than the amount of time separating two different consecutive salt additions.

The growth rate of a high salinity tolerant microalgae strain of the present invention may change during a method of the present invention. In some embodiments of the present invention, the growth rate of a high salinity tolerant microalgae strain of the present invention may be slower than and/or the substantially the same as (i.e. within about ±10%) a prior growth rate when the microalgae is subjected to a higher salinity. In certain embodiments of the present invention, the growth rate of the microalgae after the first salt addition in a series of salt additions is slower compared to the growth rate of the microalgae in the lower salinity. For subsequent salt additions, the growth rate of the microalgae may be increased compared to the first growth rate and/or substantially the same as the immediately preceding growth rate in the lower salinity. In some embodiments of the present invention, the growth rate of the microalgae declines compared to the immediately preceding growth rate when the salinity reaches about 150 ppt or more.

In certain embodiments of the present invention, a method of the present invention comprises culturing and/or growing a microalgae for a period of time prior to subjecting a microalgae to serially increased concentrations of a salt. In some embodiments of the present invention, a microalgae is grown and/or cultured in a medium for about 30 minutes or more, or any range and/or individual value therein, prior to subjecting a microalgae to serially increased concentrations of a salt. In certain embodiments of the present invention, a microalgae is grown and/or cultured in a medium for about 1, 2, 3, 4, 5, 6, 7, 8, 9, 10, 11, 12, 13, 14, 15, 16, 17, 18, 19, 20, 21, 22, 23 hours or about 1, 2, 3, 4, 5, 6, 7, 8, 9, 10, 11, 12, 13, 14, 15, 16, 17, 18, 19, 20 days or more, or any range therein, prior to subjecting a microalgae to serially increased concentrations of a salt. In some embodiments of the present invention, a method of the present invention may comprise growing a microalgae for a period of time prior to subjecting a microalgae to serially increased concentrations of a salt in a medium having a salinity in a range from about 0 ppt to about 45 ppt, or any range and/or individual value therein, such as, but not limited to about 30 ppt to about 45 ppt. In some embodiments of the present invention, a method of the present invention comprises growing a microalgae for about 14 days in a medium having a salinity in a range from about 30 ppt to about 45 ppt prior to subjecting a microalgae to serially increased concentrations of a salt.

According to some embodiments of the present invention, a salt is added to a medium to increase the salinity of the medium to a salinity in a range from about 50 ppt to about 400 ppt, thereby providing a high salinity medium. The adding of a salt to a medium to produce a high salinity may be carried out in one or more separate salt additions, thereby producing a second high salinity medium, a third high salinity medium, etc.

Methods of growing and/or culturing microalgae are known in the art and can be used for growing and/or culturing the microalgae described herein. Exemplary methods for growing and/or culturing microalgae are described in *The alga Dunaliella: biodiversity, physiology, genomics and biotechnology*; A. Ben-Amotz, J. E. W. Polle, D. V. Subba Rao, Eds. Science Publishers (2009); Ugwu et al. *Biotechnol. Letters* 27(2):75-78 (2003); Hemlata and Fatma. *Bull. Environ. Contam. Toxicol.* 83(4): 509-515 (2009); and Tran et al. *Biotechnol. Bioprocess Engineer.* 15(2) 277-284 (2010) the contents of each of which are incorporated by reference herein in their entireties. In general, a microalgae may be cultured in a liquid medium comprising nutrients, such as, but not limited to, macro- and/or micro-nutrients. In some embodiments of the present invention, a microalgae can be grown and/or cultured on agar plates. A microalgae can be grown under a light/dark regime or continuous light and supplemented with $CO_2$-enriched air. Growing of a microalgae in a method of present invention may be carried out using a natural and/or artificial light source.

According to some embodiments of the present invention, a method of the present invention may encompass large scale production of a secondary metabolite, such as a lipid biofuel, from a high salinity tolerant microalgae of the present invention. Thus, for industrial scale production of a secondary metabolite, a microalgae can be grown in large scale in, for example, photobioreactors (indoors and/or outdoors) and/or in open systems including, but not limited to ponds, raceways, and the like or any combination thereof.

Growing and/or culturing of a microalgae in a method of the present invention may comprise growing the microalgae at ambient air and/or room temperature. In some embodiments of the present invention, the carbon dioxide concentration of the environment in which a microalgae is grown may be changed and/or modified. In certain embodiments of the present invention, growing of a microalgae in a method of present invention may be carried out in an environment having a carbon dioxide concentration at atmospheric levels. In certain embodiments of the present invention, growing of a microalgae in a method of present invention may be carried out in an environment have a carbon dioxide concentration in a range from about 100 ppm to about $1\times10^6$ ppm, or any range and/or individual value therein, such as, but not limited to, from about 200 to about $1\times10^5$ ppm, about 300 ppm to about $0.5\times10^5$ ppm, about 500 ppm to about $1\times10^4$ ppm, or about 1,000 ppm to about $0.5\times10^4$ ppm. Growing of a microalgae in a method of present invention may be carried out in an environment having a carbon dioxide concentration of about 1%, 2%, 3%, 4%, 5%, 6%, 7%, 8%, 9%, 10%, 11%, 12%, 13%, 14%, 15%, 16%, 17%, 18%, 19%, or 20%. In some embodiments of the present invention, growing of a microalgae in a method of present invention may be carried out at a temperature in a range from about 5° C. to about 60° C., or any range and/or individual value therein, such as, but not limited to, from about 5° C. to about 40° C., about 20° C. to about 60° C., about 40° C. to about 60° C., about 15° C. to about 35° C., or about 20° C. to about 30° C.

Growing and/or culturing of a microalgae may comprise growing and/or culturing the microalgae for a time sufficient to produce a high salinity tolerant microalgae strain of the present invention. A method of the present invention may produce a high salinity tolerant microalgae strain in about 2 to about 14 or more days, or any range and/or individual value therein, such as, but not limited to about 3 to about 12 days, about 5 to about 10 days, or about 7 to about 9 days. In certain embodiments of the present invention, a method of the present invention may produce a high salinity tolerant microalgae strain in about 2, 3, 4, 5, 6, 7, 8, 9, 10, 11, 12, 13, 14, 15, 16, 17, 18, 19, 20, 21 days or more, or any range therein.

A method of the present invention may comprise providing an algae. In some embodiments of the present invention, the providing step may comprise obtaining an algae from a natural source (e.g., a pond, ocean, etc.) and/or a non-natural source (e.g., from the laboratory for a strain produced in the laboratory and not found in the wild). In certain embodiments of the present invention, the providing step may comprise collecting an algae and isolating a microalgae. The collecting of an algae may be carried out by any suitable method known to those of skill in the art. The isolating of a microalgae may comprise isolating one or more different species and/or strains of microalgae. In some embodiments of the present invention, the isolating of a microalgae may comprise characterizing the collected algae through visual, chemical, and/or biological characterization methods known to those of skill in the field and/or selecting the desired microalgae using chemical and/or biological selection methods known to those of skill in the field. In certain embodiments of the present invention, the isolated microalgae is used in a method of the present invention. In particular embodiments of the present invention, the isolated microalgae is subjected to serially increased concentrations of a salt, thereby producing a high salinity tolerant microalgae strain of the present invention as compared to a microalgae not subjected to serially increased concentrations of a salt.

A method of the present invention may further comprise selecting a high salinity tolerant microalgae strain of the present invention. The selecting step may be carried out after subjecting a microalgae to serially increasing salt concentrations. The selecting step can be carried out by any suitable means known to those of skill in the art. In some embodiments of the present invention, the selecting step comprises isolating and/or separating a high salinity tolerant microalgae strain of the present invention using chemical and/or biological methods know to those of skill in the art.

According to some embodiments of the present invention, a method of the present invention comprises growing a microalgae in a medium having a salinity in a range from about 30 ppt to about 45 ppt; adding a salt to increase the salinity of the medium, thereby providing a high salinity medium; and growing the microalgae in the high salinity medium, thereby producing a high salinity tolerant microalgae strain of the present invention. The microalgae may be any suitable microalgae, such as, but not limited to those described herein. The adding step may comprise serially increasing the salinity of the medium as described herein. In some embodiments of the present invention the adding step is cyclically repeated two or more times, such as, but not limited to, 2, 3, 4, 5, 6, 7, 8, 9, 10, or more times. In some embodiments of the present invention, the first and second growing steps are carried out for a time period of about 14 days.

According to some embodiments of the present invention, a method of the present invention may provide a high salinity tolerant microalgae strain that produces a secondary metabolite. Exemplary secondary metabolites include, but are not limited to, those described herein. In some embodiments of the present invention, a method of the present invention may provide a high salinity tolerant microalgae strain that produces a secondary metabolite in measurable quantities within about 24 hours. In certain embodiments of the present invention, a method of the present invention may provide a high salinity tolerant microalgae strain that excretes a secondary metabolite. The secondary metabolite may be excreted into the medium the high salinity tolerant microalgae is grown and/or cultured in. In some embodiments of the present invention, a method of the present invention provides a high salinity tolerant microalgae strain that produces a secondary metabolite having an absorbance maxima at about 230 nm and about 271 nm with a broad shoulder at about 430 nm.

A method of the present invention may further comprise extracting a secondary metabolite. The extracting step may be carried out using any suitable method. In some embodiments of the present invention, the extracting step may be carried out in a manner that does not result in killing the microalgae. In certain embodiments of the present invention, the extracting step may be carried out in a manner that kills less than about 75% of the microalgae, such as less about 70%, 60%, 50%, 40%, 30%, 20%, or 10% of the microalgae.

A further aspect of the present invention provides a method of producing a secondary metabolite comprising growing and/or culturing a microalgae in a medium having a salinity in a range from about 25 ppt to about 70 ppt and in an environment having a carbon dioxide concentration at about atmospheric levels, thereby producing the secondary metabolite. In some embodiments of the present invention the microalgae comprises a high salinity tolerant microalgae strain of the present invention. The growing and/or culturing step may be carried out as described herein.

In some embodiments of the present invention, a method of producing a secondary metabolite may comprise turning off, inhibiting, or the like production of the secondary metabolite. The turning off or inhibiting step may comprise increasing the salinity of the medium and/or increasing the carbon dioxide concentration of the environment. In certain embodiments of the present invention, a method of producing a secondary metabolite may comprising providing an algae, isolating a microalgae, and/or selecting a high salinity tolerant microalgae of the present invention, as described herein.

The present invention is explained in greater detail in the following non-limiting Examples.

EXAMPLES

Example 1

Development of a Model System to Cultivate and Sustain Native Algal Isolates

Environmental microbial samples will be (1) cell sorted and stored for identification and genomic sequencing and (2) cultivated in micro-photobioreactors under defined growth conditions to establish multimember communities. High throughput micro-bioreactors capable of mimicking the local environment from where the samples are extracted will be designed and built. Samples of local soils will be analyzed for nutrient content and chemical composition. These findings will be used to prepare defined medial for cell growth. Cultured environmental isolates and type strains will undergo analysis using metagenomics and computational systems biology to identify biologically active secondary metabolite pathways. Algal isolates will be propagated and archived for future experimental work.

Development of Mathematical Models for Optimization of Growth and Carbon Metabolite Composition for Desired Products Experimental-based model structure and parameters calibration will be conducted in order to produce a mathematical model capable of accurately describing the algae process. The model therefore will be used to optimize and design experiments towards maximum starch or lipid production in the algal isolates. Variables affecting metabolic flux driving metabolisms towards desired metabolic products will be targeted. This model will allow for the description of the mechanisms by which environmental conditions (such as pH, concentrations, temperature, light intensity) affect algal metabolism.

Isolation and Characterization of Metabolites Excreted by Novel Algal Isolates and Use of High Throughput Sequencing to Investigate Metabolic Potential of Algal Isolates Metabolites from microbial isolates will be extracted and characterized using liquid chromatography/mass spectroscopy (LC/MS) and gas chromatography/mass spectroscopy (GC/MS) or other appropriate techniques to identify compounds excreted by microbial isolates. Isolated algal from both cell sorting and cultivation efforts will undergo genome sequencing using Roche 454 or Solexa Illumina sequencing technology. The genomic information will allow for a database of members of the microbial community. Bioinformatics tools will be used to mine known algal genomes for molecular pathways involved in production of metabolites identified in samples. This database will allow for identification of potential metabolic pathways involved in substrate degradation, small molecule utilization, and environmental interactions.

Example 2

On two sampling trips, algae samples were collected from desert water pools near Baniyas city in the mid-region of Abu Dhabi Emirate. One native microalgae strain was successfully isolated from a water sample collected in the second sampling trip. In the laboratory, algae samples were cultivated in batch macro-photobioreactors using synthetic seawater as growth medium with added nitrogen and phosphorus nutrients, using full-spectrum florescent lights, sparging ambient/house air, and at ambient room temperature. Different growth medium salinities were used in separate photobioreactors to test the salinity limits of algae isolate growth. FIG. 1 shows the algae tubular photobioreactors in use, operated semi-batch at different salinities.

Salinity of the growth medium was originally at 33 ppt, and then increased in steps to 50 ppt, 75 ppt, 100 ppt, and 125 ppt by addition of only sodium chloride to ensure equal nutrients concentrations. Algae grew in all tested salinities, where the lag phase lasted longer when the algae was first introduced to a new salinity than in the following dilutions. Another observation is that in some cases, algae's color shifted to an orange shade when growth medium was reduced due to evaporation, which without wishing to be limited to any particular theory might indicate activation of secondary metabolites, and without wishing to be limited to any particular theory possibly accumulation of carotenoids. Algae samples were inspected regularly under the microscope, and no invasive strains were observed. DNA was extracted from, two normally grown algae samples at 33 ppt and 75 ppt, and from a stressed sample at 33 ppt. The extracted DNA was cryogenically stored and will be sent for sequencing to identify the isolated wild algae strain.

A preliminary general algae growth model was built using a MATLAB/EXCEL simulation package that requires minimum programming experience. The model is based on a continuous chemostat photobioreactor with an integrated set of growth, decay, charge balance, and gas/liquid mass transfer equations and stoichiometry from Equation 1 to include key variables and products as needed. The algae growth and decay in a chemostat photobioreactor are as follows:

$$\frac{d}{dt}X_{alg} = (\mu - d - D)X_{alg} \quad (2.2.1)$$

$$\mu = \mu_m F(I) F(N) \quad (2.2.2)$$

$$F(I) = \frac{I}{I_s} e^{1 - \frac{I}{I_s}} \quad (2.2.3)$$

$$F(N) = \frac{S_C}{K_C + S_C} \frac{S_N}{K_N + S_N} \frac{S_P}{K_P + S_P} \quad (2.2.4)$$

$$D = \frac{Q}{V_r}, \quad (2.2.5)$$

where $$\frac{d}{dt}X_{alg}$$

is the algal biomass growth rate in chemostat photobioreactor ($gC \cdot L^{-1} \cdot d^{-1}$);

$\mu$ is the specific growth rate ($d^{-1}$);

d is the algae decay rate ($d^{-1}$);

D is the dilution rate ($d^{-1}$);

$X_{alg}$ is the instantaneous concentration of alive algae biomass ($gC \cdot L^{-1}$);

$\mu_m$ is the maximum phototrophic growth rate ($d^{-1}$);

F(I) is the light intensity function, $0 \leq F(I) \leq 1$;

F(N) is the nutrient monod function, $0 \leq F(N) \leq 1$;

I is the actual light intensity (mol photon$\cdot m^{-2} \cdot s^{-1}$);

$I_s$ is the saturation light intensity (mol photon$\cdot m^{-2} \cdot s^{-1}$);

$S_{C,N,P}$ is the nutrients concentration ($g \cdot L^{-1}$);

$K_{C,N,P}$ is the nutrients half saturation concentration ($g \cdot L^{-1}$);

Q is the volumetric flow rate in ($m^3 \cdot h^{-1}$); and $V_r$ is the photobioreactor volume ($m^3$).

Figure 2:
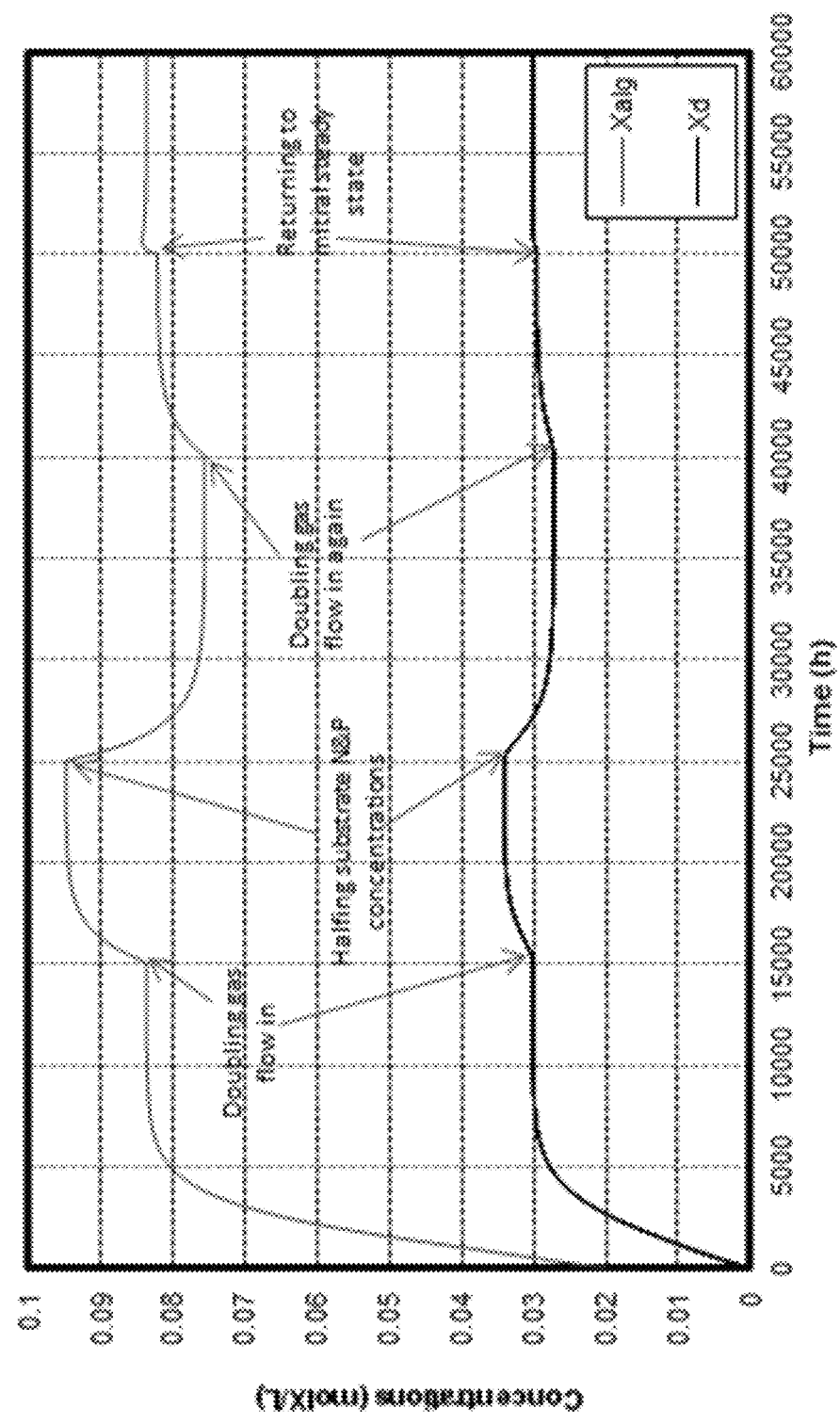
FIG. 2 shows the simulated algae biomass growth in a chemostat open raceway pond vs. time at different steady states.

Using the SWAMCO ecological model for algae growth kinetics, coupled with a set of assumed open raceway pond dimensions and with changing operating data, the simulation package ran the model and different steady-states were achieved. FIG. 2 illustrates the change in both active and decayed algae biomass concentrations in the reactor with time at different steady states.

Example 3

Directed Evolution of Salinity Growth Profile

A native microalgae strain was isolated from a desert in the United Arab Emirates. A directed evolution growth profile was performed to determine the maximum salinity for the algae. The 300 ppt range is around 5.5 M (solubility in water is 350 ppt). This is approximately nine times saltier than the open ocean and approximately seven times saltier than the Arabian Gulf. The growth characterization of the algae is shown in Table 1, and shows if a secondary metabolite was produced for each salinity growth condition. The growth experiments took from 5 to 10 days to complete each.

TABLE 1

Growth characterization of the algal isolate under varying salinity conditions.
Growth characterization of algael isolate

| Salt Concentration - ppt | [CO2] Atmospheric | Metabolite Production |
|---|---|---|
| 33 | yes | yes |
| 55 | yes | yes |
| 75 | yes | no |
| 100 | yes | no |
| 125 | yes | no |
| 150 | yes | no |
| 300 | yes | no |

Carbon Dioxide Concentration Tolerance

An experiment conducted at 25° C. and 33 ppt salinity demonstrated that the microalgae grows in a carbon dioxide ($CO_2$) atmosphere ranging from 300 ppm to $1.0 \times 10^5$ ppm (10% $CO_2$ atmosphere). At 12% $CO_2$ atmosphere the isolated microalgae exhibits stunted growth falling below the threshold limit for growth detection at this time. The results of the carbon dioxide concentration tolerance are shown in Table 2, which shows if a secondary metabolite was produced for each $CO_2$ concentration.

TABLE 2

Growth of the algae in 33 ppt salt under varying $CO_2$ concentrations.
Metabolite production at 33 ppt salt growth media

| [CO2] | Metabolite Production |
|---|---|
| atmospheric | yes |
| 2% | no |
| 4% | no |
| 6% | no |
| 8% | no |
| 10% | no |
| 12% | no |

Isolation and Characterization of Excreted Secondary Metabolite

Figure 3:
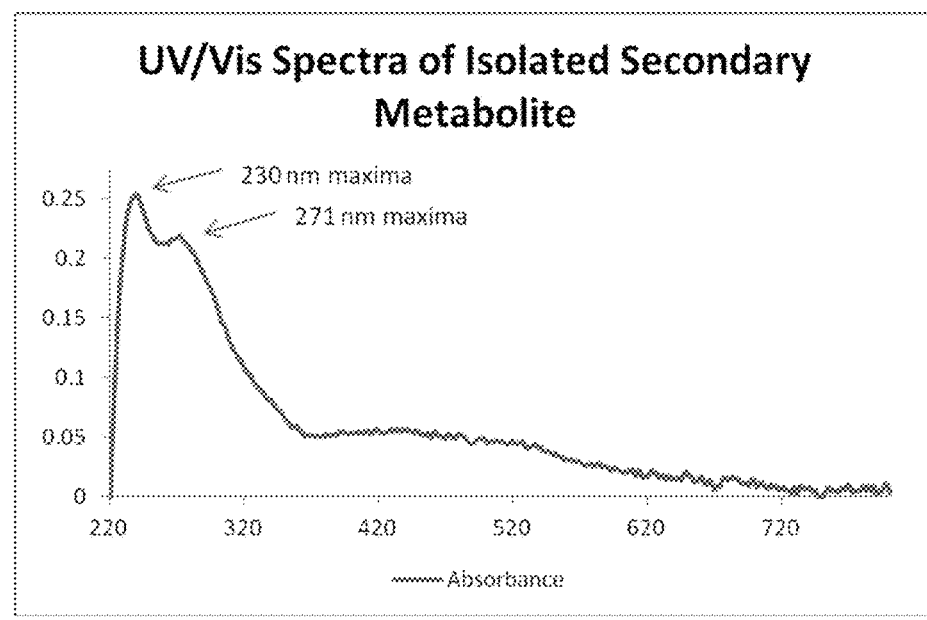
FIG. 3 shows the UV/Vis spectra of the isolated secondary metabolite excreted in algae growth media.

A secondary metabolite is excreted into the growth media and is highly soluble. Without wishing to be limited to any particular theory, this suggests that the excreted secondary metabolite is not a carotenoid as carotenoids are not soluble and are found in vesicles in algae. A UV/Visible spectrum of the compound shows an absorbance maxima at 230 nm and 271 nm. In contrast, absorption spectra maxima for carotenoids range from 444 nm to 472 nm. The absorption maximum at 230 nm is characteristic of a conjugated carbon network and the 271 nm maxima are characteristic of a cyclic molecule such as an amino acid side chain or a base. FIG. 3 shows the UV/Vis spectra of the secondary metabolite excreted in algae growth media.

Methanol extraction precipitates the secondary metabolite. Acetonitrile and hexane extraction partitions and concentrates the metabolite into the aqueous phase. In contrast to carotenoids or other non-polar molecules that partition into the organic extraction phase. Further characterization of the excreted metabolite will be pursued using Fourier transform infrared spectroscopy (FTIR), liquid chromatography with tandem mass spectroscopy (LC/MS) and gas chromatography with tandem mass spectroscopy (GC/MS). The results from these characterizing experiments will provide key information regarding the structure and connectivity of the atoms that compose the secondary metabolite.

Development of Method for Production, Excretion, and Purification of Excreted Metabolite.

The experiments performed show that the production and excretion of the excreted secondary metabolite is affected by the concentration of $CO_2$ available as a carbon source in the growth media and the salinity of the growth media. At atmospheric $CO_2$ concentration and 33 or 55 ppt salt, there is production of the secondary metabolite, where at higher concentrations of salinity (>75 ppt) there is no measurable production of the excreted metabolite. At $CO_2$ concentrations of 2% or higher the algae will not produce the secondary metabolite at either 33 ppt or 55 ppt salt (See, Tables 1 and 2).

Genomic Identification and Characterization of Algae Species

Genomic sequencing of the algae species will be performed and will allow for the identification of the algae species.

Example 4

Figure 4:
FIG. 4 shows a light microscope image of an isolated microalgae at 33 ppt under 1000× magnification.
Figure 5:
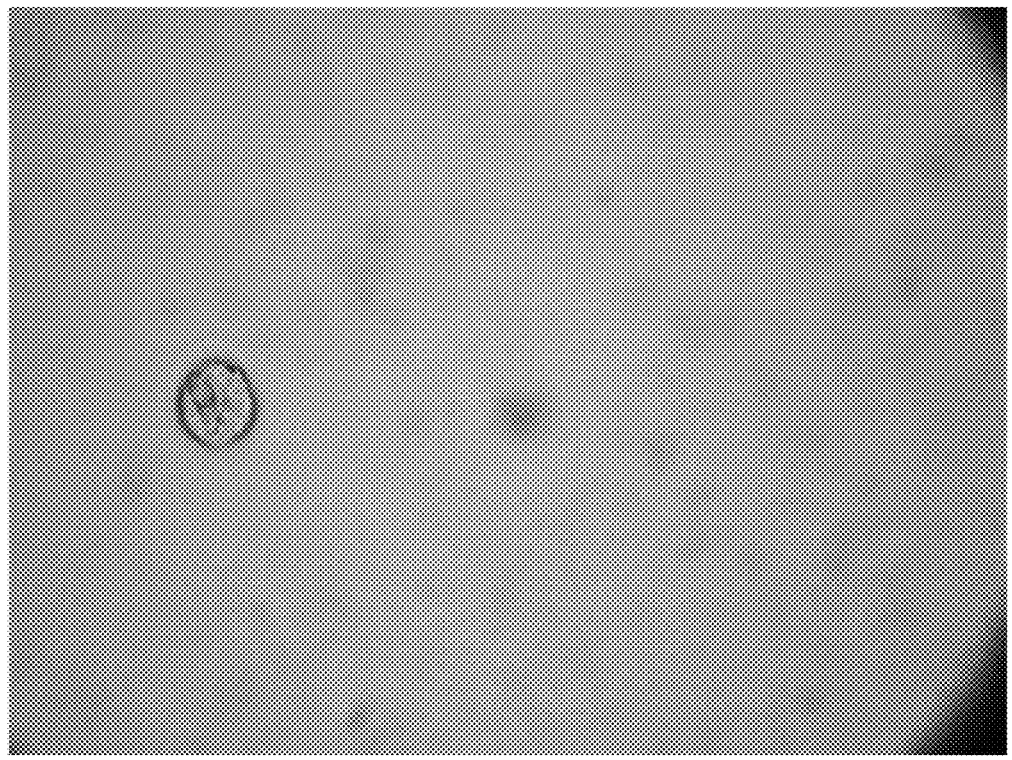
FIG. 5 shows a light microscope image of an isolated microalgae at 50 ppt under 1000× magnification.
Figure 6:
FIG. 6 shows a light microscope image of an isolated microalgae at 75 ppt under 1000× magnification.
Figure 7:
FIG. 7 shows a light microscope image of an isolated microalgae at 100 ppt under 1000× magnification.

Images of a microalgae produced by a method of the present invention were taken at various salinity concentrations. FIG. 4 shows an isolated microalgae at 33 ppt. FIG. 5 shows an isolated microalgae at 50 ppt. FIG. 6 shows an isolated microalgae at 75 ppt. FIG. 7 shows an isolated microalgae at 100 ppt.

Example 5

On two sampling trips, algae samples were collected from desert water pools near Baniyas city in the mid-region of Abu Dhabi Emirate. One native microalgae strain was successfully isolated from a water sample collected in the second sampling trip. Microalgae samples were cultivated in tubular batch macro-photobioreactors (2.4 L) (AquaMedic, Germany), at 25° C. using aquarium synthetic sea salts solution (Mariscience Int. Co. Thailand) as growth medium supplemented with nitrogen and phosphorus nutrients, using full-spectrum florescent lights, sparging ambient/house air, and at ambient room temperature. Growth medial consisted of 40 g/L of sea salt solution (final concentration 33 ppt salinity). Successive growth media preparations were supplemented with NaCl (Sigma Int. UK) to a final salinity of 50 ppt, 75 ppt, 100 ppt, 125 ppt, 150 ppt, and 300 ppt.

After 14 days of growth, 5% algae growth samples were passaged stepwise into higher salinity growth media until a final growth concentration of 300 ppt salt growth media was obtained. Cell growth was monitored using a combination of optical density measurements (680 nM and 735 nM) and microscopic cell counting techniques. Samples were stored at 4° C. and −80° C. for subsequent analysis, DNA extraction, and strain records.

After the $3^{rd}$ passage into 33 ppt and 50 ppt growth media, it was observed that the microalgae isolate began producing and excreting a red colored highly soluble compound into the growth media. Initial purification steps were performed using a modified Hagerthey et. al. method (Journal of Phycology 42 (2006) 1125-1136.). In short a 100% methanol, 100% acetonitrile and hexane extraction were performed on filtered supernatant to isolate excreted compound.

The expression of the excreted compound at 33 ppt growth media was studied in a set of 14 day experiments were conducted with a concentration of ambient, 2%, 4%, 8%, 10%, and 12% $CO_2$ concentration sparging air. In addition, growth experiments were conducted using a 400 ml bioreactor (Photosystems Instruments, Czech Republic) where isolated micro algae was grown for 1 week under 500 ppm $CO_2$ and remaining sparging air consisting of 22% $O_2$ 78% $N_2$ mixture until media became red brown in color. After 1 week growth, the concentration of $CO_2$ in sparging air was changed to 2% of total volume. The concentration of $CO_2$ during the extent of the experiment was monitored using GMS 150 gas mixing system (Photosystems Instruments, Czech Republic). Growth characterization of the isolated algae and metabolite production are the same as those set forth in Tables 1 and 2.

Genomic DNA was extracted from three isolated algae samples; a 33 ppt and a 75 ppt salinity samples grown under full nutrient media and one sample grown at 33 ppt salinity grown under stressed conditions. The genomic DNA extraction was performed using an Ultraclean Microbial DNA Isolation Kit as per manufactures instructions (MoBio, California, US). Genomic DNA samples were sent to the Bio-Micro Sequencing Center MIT, Cambridge, US) for genomic sequencing.

Results

Different growth medium salinities were used in separate photobioreactors (FIG. 1) to test the salinity limits of algae isolate growth. Salinity of the growth medium was originally at 33 ppt, and then increased in steps to 50 ppt, 75 ppt, 100 ppt, 125 ppt, 150 ppt, and 300 ppt by addition of only sodium chloride (NaCl) to ensure equal micronutrients concentrations from the synthetic sea salts. On initial passage to a higher salinity, the algae isolate's rate of growth was much slower than the previous lower salinity growth. Upon subsequent passages, the growth activity increased and upon the third or fourth passage, the growth rate for the higher salinity matched the previous salinity. This trend was seen until the growth media salinity was at 150 ppt. At 300 ppt salinity, the growth of the microalgae isolate was severely affected.

Algae samples were inspected regularly using light microscopy for cell counting and to monitor samples for evidence of invasive strains. During the growth of the algae, no invasive strains were observed. One observation under the microscope was that at 100 ppt salinity the algae cells began to change morphology with the appearance of an extracellular polymeric substance (EPS). While not wishing to be bound to any particular theory, it is hypothesized that the increase in EPS under saline stress confers the ability of algae strains to buffer it's immediate environment and thus survive the osmotic stress of the saline environment [16, 17].

Another observation is that in lower salinities, algae's growth medial color shifted to red brown shade, which suggests an activation of an excreted highly soluble secondary metabolite. Optical spectra of the isolate in growth media exhibited maxima at 231 nm and at 271 nm with a broad shoulder at 430 nm (FIG. 3). While not wishing to be bound to any particular theory, these data suggest that the metabolite contains a hyperconjugated cyclic composition. From literature data, the assumption was made that the metabolite could be a novel carotenoid derivative [19-21]. This assumption was rapidly discarded as several lines of data contradicted what is known about carotenoid properties [22, 23]. Light microscopy confirmed that the effect of the color change was in the media and not in the cells, as the cells from the growth media did not exhibit a change in color. Initial extraction experiments did not partition the metabolite into the organic phase. In addition, after each passage the cells did not exhibit evidence of metabolite excretion until after 24-36 hours of growth.

The ability to control the production and excretion a secondary metabolite is highly significant. These experiments show that by changing the concentration of $CO_2$ in the sparging air the algae will excrete or consume the produced metabolite. In addition, this algae strain has the capacity to grow at elevated $CO_2$ concentration In order to identify the isolated algae strain, DNA was extracted from, two normally grown algae samples at 33 ppt and 75 ppt, and from a stressed sample at 33 ppt. The extracted DNA was sent to the BioMicro Sequencing Center where current genomic sequencing is being done to determine the genomic content of the isolated algae species.

Recent increases in energy demands by rapidly growing economies are driving the need for new sources of fuel. To date, the most common source of fuel has been based on fossil fuel derived fuels. This growing need for fuel has to be balanced with the understanding that the release of $CO_2$ into the atmosphere by the use of fossil fuels is not a sustainable option for long-term energy demands. Bio-based fuels can provide an alternative source of energy to drive growing economies. These bio fuels can be readily incorporated into existing infrastructure. Existing drawbacks for use of most biofuels are the use of valuable agricultural land for production, competition for food, and use of potable water for growth.

Saline tolerant algae is a viable alternative source for biofuel production. They can be grown in non-arable lands and can use seawater or other non-potable water as a source for cultivation of algae. The algae strain isolated in this work meets the prerequisites for a source of biofuels.

The ability of this strain to grow under a great range of salinities makes it an ideal candidate for use in large-scale raceway ponds. This strain is ideal for growth along coastlines where the soil salinity is elevated due to tidal flows and thus making the land unusable for agricultural ventures. In addition, the strain is able to withstand large changes in water salinity driven by evaporation of water from raceway ponds.

The production of high value products by algae, such as secondary metabolites used as nutritionals, as chemical feedstocks, and as pharmaceuticals provide an added value to the cultivation of algae for biofuels. These secondary metabolites can have a significant impact on the overall lifecycle cost of production of biofuels from algae species. This isolated strain has the capacity to produce a yet structurally identified metabolite by adjusting the composition of the sparging air.

REFERENCES

[1] B. Petroleum, Statistical Review of World Energy 2012, British Petroleum, 2012.
[2] J. C. R. Hunt, S. E. Belcher, Y. V. Timoshkina, in: H. J. S. Fernando, Z. Klaie, J. L. McCulley (Eds.), Springer Netherlands, 2012, pp. 25-37.
[3] Y. Ghasemi, S. Rasoul-Amini, A. Naseri, N. Montazeri-Najafabady, M. Mobasher, F. Dabbagh, Applied Biochemistry and Microbiology 48 (2012) 126-144.
[4] Y. Chisti, Biotechnology Advances 25 (2007) 294-306.
[5] T. M. Mata, A. A. Martins, N. S. Caetano, Renewable and Sustainable Energy Reviews 14 (2010) 217-232.
[6] U. DOE, National Algal Biofuels Technology Roadmap, in: O.o.E.E.a.R.E.U.S. Department of Energy, Biomass Program (Ed.), 2010.
[7] S. A. Khan, Rashmi, M. Z. Hussain, S. Prasad, U. C. Banerjee, Renewable and Sustainable Energy Reviews 13 (2009) 2361-2372.
[8] P. Spolaore, C. Joannis-Cassan, E. Duran, A. Isambert, Journal of Bioscience and Bioengineering 101 (2006) 87-96.
[9] T. Mutanda, D. Ramesh, S. Karthikeyan, S. Kumari, A Anandraj, F. Bux, Bioresource technology 102 (2011) 57-70.
[10] S. K. Ratha, R. Prasanna, Prikladnaia biokhimiia i mikrobiologiia 48 (2012) 133-149.
[11] L. Brennan, P Owende, Renewable and Sustainable Energy Reviews 14 (2010) 557-577.
[12] A. W. D. Larkum, I. L. Ross, O. Kruse, B. Hankamer, Trends in biotechnology 30 (2012) 198-205.
[13] D.o.E.a.S. Affairs, World Population to 2300, United Nations, 2004.
[14] S. E. Hagerthey, J. William Louda, P. Mongkronsri, Journal of Phycology 42 (2006) 1125-1136.
[15] A. Kumar, E. A. El Gawad, Geography of Abu Dhabi Emirate, United Arab Emirates, in: E.A.A. Dhabi (Ed.), Environmental Agency, Abu Dhabi, 2008.
[16] H. Liu, E. J. Buskey, Journal of Phycology 36 (2001) 71-77.
[17] A. Mishra, B. Jha, Bioresource technology 100 (2009) 3382-3386.
[18] S. Ozturk, B. Aslim, Environmental Science and Pollution Research 17 (2010) 595-602.

[19] M. Hejazi, C. De Lamarliere, J. Rocha, M. Vermue, J. Tramper, R. Wijffels, Biotechnology and bioengineering 79 (2002) 29-36.
[20] C. R. Sarkar, L. Das, B. Bhagawati, B. C. Goswami, Asian Journal of Plant Science and Research 2 (2012) 546-549.
[21] F. Delgado-Vargas, A. Jimenez, O. Paredes-Lopez, Critical Reviews in Food Science and Nutrition 40 (2000) 173-289.
[22] S. Takaichi, Marine drugs 9 (2011) 1101-1118.
[23] E. Christaki, E. Bonos, I. Giannenas, P. Florou-Paneri, Journal of the Science of Food and Agriculture (2012).

Example 6

An algae strain, AAH001, was derived from a wild type strain isolated from a desert water hole in the Abu Dhabi Emirate. The AAH001 strain was evolved through sequential steps in order to be able to grow under high salinity conditions. The wild type strain, as isolated, proved incapable of living in salinities higher than 150 ppt.

The AAH001 high saline strain was evolved to grow at increasing salinities by sequential increase of media salinity through controlled desiccation of growth media. The sequential steps of increasing salinity were of 50 ppt. The initial media was prepared using artificial sea salt made by Mariscience Int'l Co., Ltd. and the salinity of the media was increased using sodium chloride for each 50 ppt increase. The AAH001 strain was allowed to evolve at the new salinity for 2-3 passages composed of growth between $1\times10^8$-$1\times10^9$ cells per ml followed by a 15% dilution of the growth media with fresh growth media at the current salinity. After passages and growth under a new salinity condition, the salinity of the last passage (between $1\times10^8$-$1\times10^9$ cells per ml), the growth media was allowed to increase in salinity through controlled desiccation. The controlled desiccation was achieved by evaporation of the growth media over a period of up to 2 weeks until the desired salinity was obtained and then the algae strain growth media was supplemented with fresh media up to a final volume of 2.4 liters at the new salinity. The process was repeated as described above.

This process was repeated until growth of the AAH001 strain was achieved at 300 ppt salinity. A higher salinity growth media was not achievable due to the precipitation of media salts in the growth container. The evolved strain of AAH001 was back tested to see if it would grow at the original salinity of the wild type strain, which was between 50-60 ppt, and it was determined that the AAH001 strain maintained the original growth characteristics of the wild type strain. The growth of AAH001 under increasing salinity was monitored by measuring turbidity and final visual cell count.

A resampling of the wild type strain from the original desert water hole demonstrated that the wild type strain was able to grow in the laboratory at low salinities, but not at salinities over 150 ppt as shown in Table 3.

TABLE 3

Comparison of the growth of the wild type algae strain and AAH001 strain at different salinities; "+" indicates growth and "−" indicates no growth.

| Salinity (ppt) | Wild Type | AAH001 |
|---|---|---|
| 33 | + | + |
| 50 | + | + |
| 75 | + | + |
| 100 | + | + |
| 125 | + | + |
| 150 | + | + |
| 200 | − | + |
| 250 | − | + |
| 300 | − | + |

Example 7

Temperature profile characterization experiments were performed on the AAH001 strain using a PSI-FMT-150 photobioreactor (0.45 L), which is a highly controllable photobioreactor where temperature and light intensity are easily manipulated. The PSI-FMT-150 was connected to a PSI-GMS-150 gas mixing system that controls the flow rate and composition of the sparged gases. The PSI-FMT-150 can be operated in both batch mode and chemostat mode, where a peristaltic pump (PSI-PP-500) is attached for the chemostat mode. The PSI-FMT-150 has the capacity to measure temperature, pH, $OD_{680}$, $OD_{735}$, fluorescence, and oxygen content at a rate of one reading per minute.

The $OD_{735}$ represents the measurement of cells, while $OD_{680}$ represents the measurement of cells plus the chlorophyll photosynthetic pigments, which means that as the difference between $OD_{680}$ and $OD_{735}$ increases, more photosynthetic pigments are active. However, these measures may vary with the photosynthetic pigments profile.

In this experiment, PSI-FMT-150 was run in chemostat mode, using growth media salinities of 33 ppt and 100 ppt at a 0.175 ml/min, sparging 0.25 l/min compressed air enriched with 0.5% $CO_2$, and under a 390 µmol(photon)·$m^{-2} \cdot s^{-1}$ light intensity. A steady state was achieved at 25° C. before the experiment was started, then the temperature was increased by 5° C. every 24 hours from 25° C. up to 50° C.

Figure 8A:
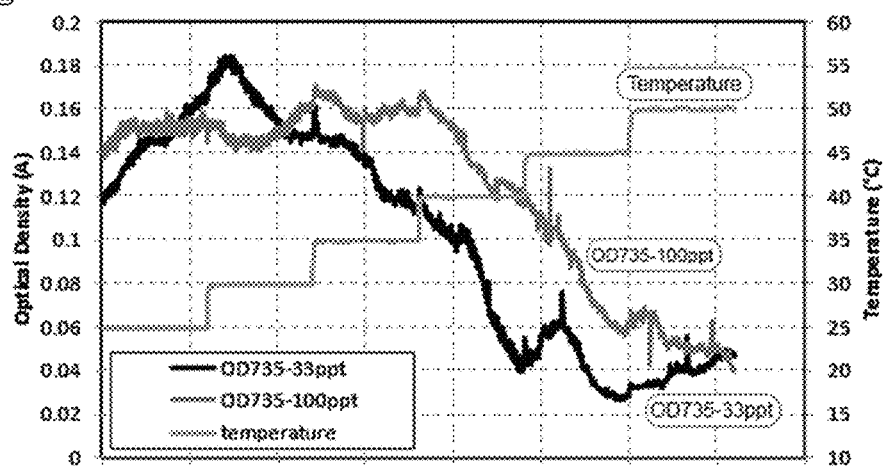
FIGS. 8A-8C.
Figure 8B:
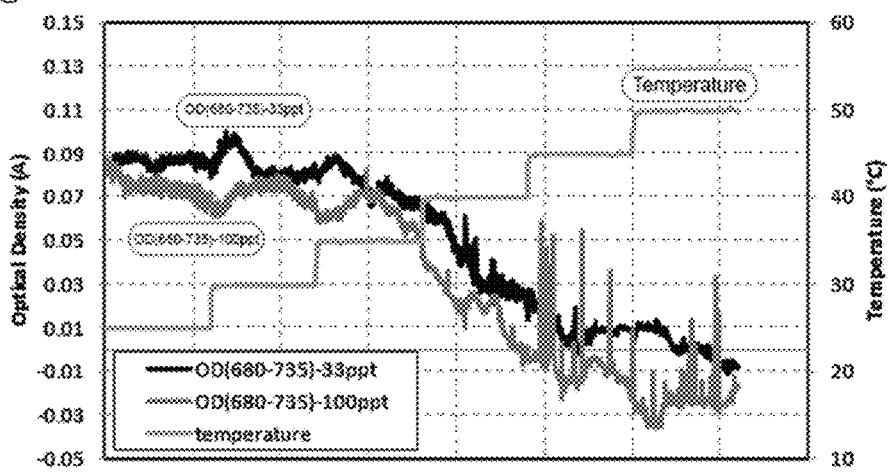
Figure 8C:
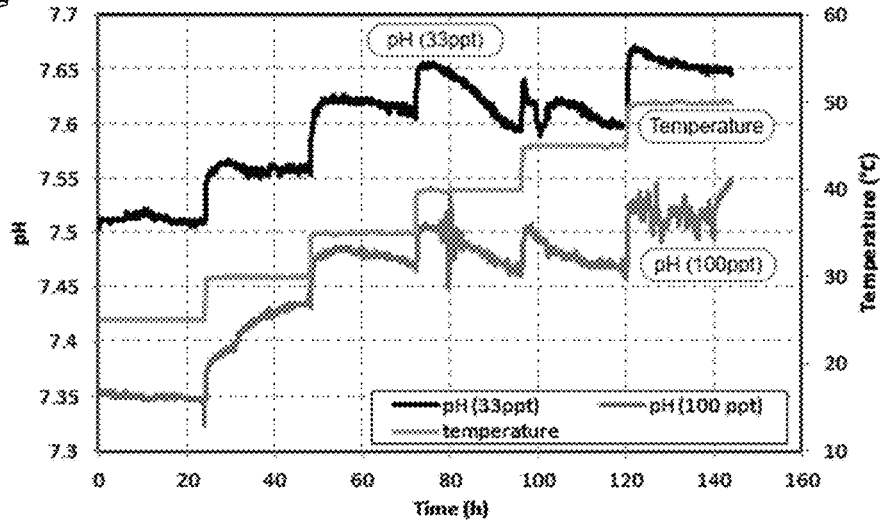

FIGS. 8A and 8B show the optical density profiles from the ascending temperature experiments. As shown in FIG. 8A, higher salinity increases the temperature optima for the strain. For the 33 ppt growth media, the maximum growth occurred during the 30° C. step. On the other hand, the optical density for the 100 ppt didn't subside until the 40° C. step. Moreover, FIG. 8B shows a significant drop in the optical density for photosynthetic centers in the 35° C. step for both salinities. FIG. 8C shows the pH profile from the ascending temperature experiments.

Example 8

Under low salinity growth conditions, a produced secondary metabolite is excreted from both the wild type strain and the AAH001 strain into the growth media, which contains many salts, ions, and other metabolites that might be dissolved in the media, thus making it fairly difficult to isolate the red-colored secondary metabolite. Different methods were tried to isolate the desired secondary metabolite, where each method yielded different results.

The first method used involved mixing the growth media containing the red-colored secondary metabolite with organic solvents such as acetonitrile and hexane. The secondary metabolite stayed in the aqueous phase. Thus, without wishing to be bound to any particular theory, it is believed that the secondary metabolite is hydrophilic.

The second method used involved adding the growth media to methanol in a 1:4 ratio, where a slight exothermic reaction was observed that released a minute amount of gas and resulted in the precipitation of many salts along with the red-colored metabolite. Sufficient amounts of the precipitate were prepared, washed with methanol, and dried to produce a purple-colored powder. The same method was used on fresh growth media, and a white precipitate was formed. Thus, without wishing to be bound to any particular theory, it is believed that the purple-colored powder contained other compounds with the red-colored metabolite. The purple-colored powder was then used in further methods to isolate the secondary metabolite.

Figure 9:
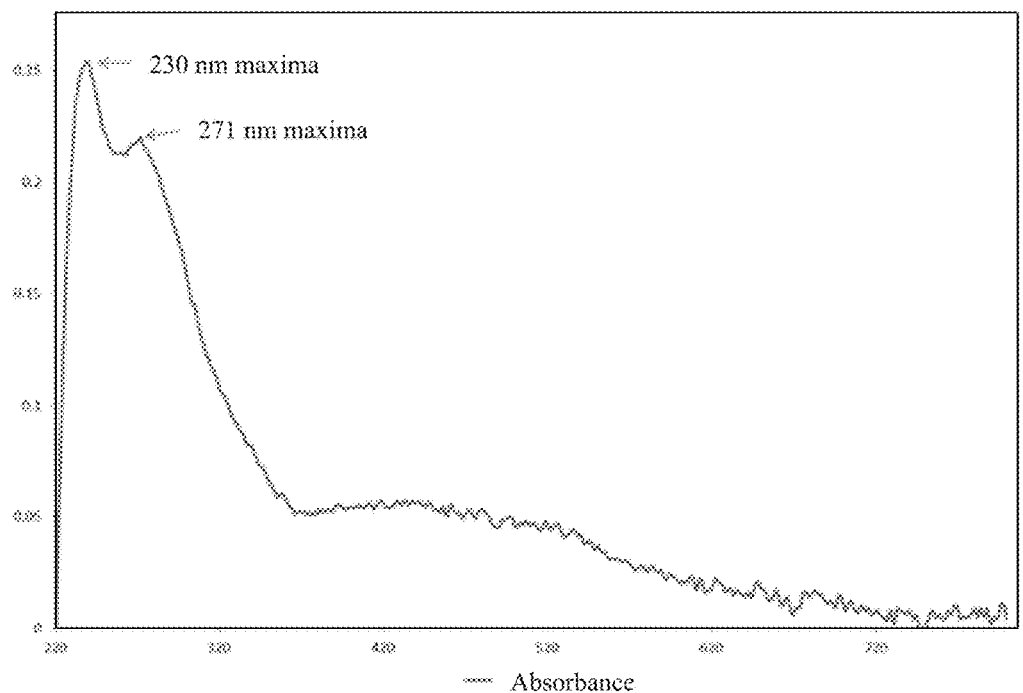
FIG. 9 shows a UV/Visible spectra of an isolated secondary metabolite from algae growth at ambient $CO_2$ concentration under 33 ppt and 50 ppt salinity.

The first experiment done with the powder was a mild acid hydrolysis. An 8% sulphuric acid in water solution was made, where the powder was dissolved, and the result was a yellow-colored solution. When the yellow solution was autoclaved, dark-red flakes formed in the solution. These were difficult to extract and didn't settle even under centrifugation. A High-Performance Liquid Chromatography (HPLC) sugar analysis was performed using the yellow solution, and no sugars, such as glucose and arabinose, were found by comparing against a sugars database. A UV spectrum was taken for the powder dissolved in water as shown in FIG. 9, where two maxima are present at 230 nm and 271 nm, which without wishing to be bound to any particular theory might indicate aliphatic and aromatic bonds hyper conjugation.

Further work was done to try to isolate the secondary metabolite by crystallization. The solubility of the purple-powder isolated was tested in solvents with varying ionic and hydrophobic characteristics to determine the optimal solvent for crystallization. The isolated powder was fully soluble in 10% trifluoroacetic acid in water solution, where the color of the solution turned into orange as the powder dissolved. The powder was semi soluble in DMSO and in water. The powder was not soluble in DMF, methanol, ethanol, and trifluoroacetic acid, acetonitrile, diethyl ether, and diisopropyl ether.

After initial optimization of solvents, crystallization by slow diffusion was set up using powder solutions and varying diffusive solvents. As summarized in Table 3, the solution pairs resulting in crystallization of the secondary metabolite are 10% trifluoroacetic in water with either ethanol or diethyl ether. The crystals were separated and used for further analysis to identify the secondary metabolite

TABLE 4

Slow diffusion solvent pairs used to crystallize the secondary metabolite excreted by the algae strain.

| Principal Solvent | Solvent Pair Used | Crystals formed? |
|---|---|---|
| DMSO | Methanol | No |
|  | Diethyl ether | No |
|  | Diisopropyl ether | No |
| 10% Trifluoroacetic + 90% water | Methanol | No |
|  | Ethanol | Yes |
|  | DMF | No |
|  | Diethyl ether | Yes |
|  | Acetonitrile | No |

Figure 10:
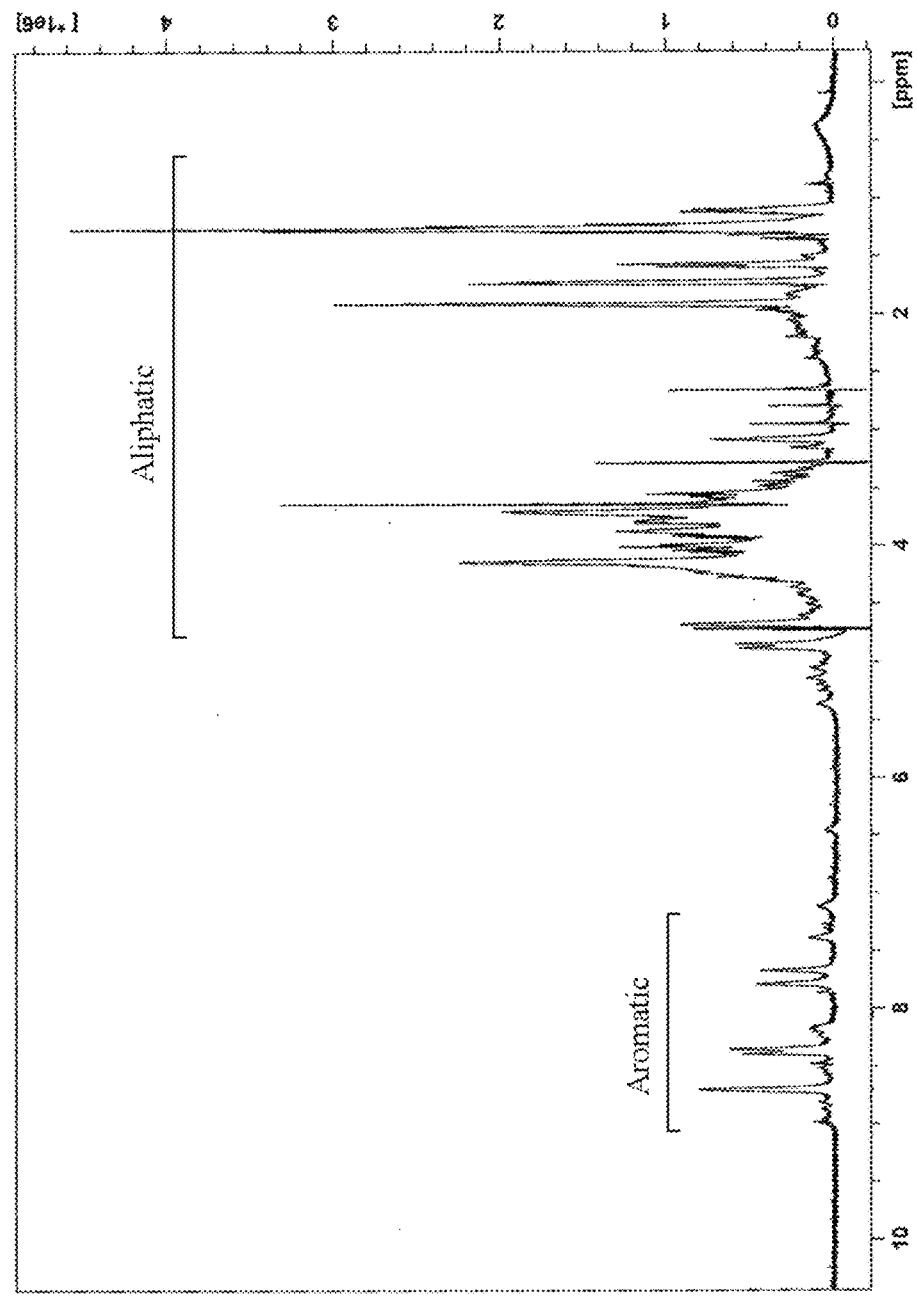
FIG. 10 shows a H-NMR spectra of an isolated secondary metabolite.

The characterization was continued by subjecting the isolated crystals to nuclear magnetic resonance (NMR) analysis. The H-NMR spectra of the isolated compound exhibited H-shift characteristic of an aromatic ring as shown in FIG. 10. In addition the spectrum displays evidence of aliphatic side chains in the molecule. The molecular characterization of this molecule is ongoing.

Example 9

Fatty Acid Methyl Ester (FAME) analysis was conducted on three different samples of the AAH001 strain. The objective of FAME analysis was to quantitatively and qualitatively analyze the lipid contents of the algae strain. The three samples were cultivated in 33 ppt growth media using compressed air with 0%, 3%, and 6% $CO_2$ enrichment. FAME analysis was then conducted on the samples.

The results from the analysis with the AAH001 strain were then compared against a *Nannochloropsis salina* sample as a quality control sample. Table 4 summarizes the results of the FAME analysis.

TABLE 5

Results from the FAME analysis.

| Sample FAME (% DW) | Sample #1 (0% CO2) | Sample #2 (3% CO2) | Sample #3 (6% CO2) | QC Nanno |
|---|---|---|---|---|
|  | 32.36 ± 0.25 | 19.43 ± 0.22 | 11.65 ± 0.15 | 9.41 ± 0.05 |
| C8 | 0.00 | 0.00 | 0.00 | 0.51 |
| C10 | 0.00 | 0.00 | 0.00 | 0.41 |
| C12 | 0.00 | 0.00 | 0.00 | 0.55 |
| C14 | 0.65 | 0.70 | 1.06 | 5.27 |
| C16:3 | 2.49 | 1.15 | 3.23 | 0.81 |
| C16:4 | 0.82 | 1.10 | 1.20 | 0.80 |
| C16:2 | 2.99 | 1.21 | 1.80 | 0.00 |
| C16:1n9 | 0.24 | 1.32 | 1.89 | 35.83 |
| C16:1 | 1.79 | 4.45 | 4.09 |  |
| C16:1n11 | 0.11 | 0.12 | 0.36 | 2.54 |
| C16 | 35.97 | 36.91 | 34.12 | 23.61 |
| C18:2 | 8.57 | 8.12 | 7.67 | 2.38 |
| C18:1n9 | 38.77 | 22.39 | 22.92 | 3.62 |
| C18:3 | 4.04 | 14.09 | 9.50 | 0.43 |
| C18 | 1.10 | 0.68 | 1.02 | 0.27 |
| C20:4 | 0.85 | 0.45 | 1.78 | 4.06 |
| C20:5 | 1.14 | 5.88 | 6.87 | 18.89 |
| C20 | 0.20 | 0.36 | 1.53 | 0.00 |
| C22:1n9 | 0.00 | 0.11 | 0.17 | 0.00 |
| C22 | 0.00 | 0.11 | 0.00 | 0.00 |
| C24 | 0.27 | 0.85 | 0.78 | 0.00 |

As can be seen from Table 4, the FAME results for the native strain AAH001 show a decrease in total lipids content as $CO_2$ enrichment increases. Moreover, the lipids profile for the native strain differs from the quality control *Nannochloropsis salina* sample in both lipids content and fatty acids profile.

Of note, the AAH001 strain makes approximately 32% fatty acids under environmental $CO_2$ conditions. In general, most other strains have to be supplemented with $CO_2$ and starved for a particular nutrient, such as nitrogen, in order to achieve a fatty acid content that is near these results. In addition, the concentration of fatty acids in the cell of the AAH001 strain is the optimal concentration at which the production of fuels from algae becomes a commercially viable option.

Example 10

The strain AAH001 was cultivated successfully at a maximum salinity of 300 ppt. Successful cultivation was defined by an increase in optical density over time and a growth of more than two orders of magnitude over the growth period as determined by endpoint visual cell counting using microscope and hemocytometer. The salinity was increased in steps until sustained growth was achieved at a salinity of 300 ppt. More steps will be added to test for growth at higher salinities.

FIGS. 11A-F show fluorescent microscopy images of the isolated wild-type strain and the AAH001 strain at 460× magnification.

The foregoing is illustrative of the present invention, and is not to be construed as limiting thereof. The invention is defined by the following claims, with equivalents of the claims to be included therein. All publications, patent applications, patents, patent publications, sequences identified by GenBank and/or SNP accession numbers, and other references cited herein are incorporated by reference in their entireties for the teachings relevant to the sentence and/or paragraph in which the reference is presented.

That which is claimed is:

1. A method of producing a high salinity tolerant microalgae strain comprising:

subjecting a microalgae cell in a medium to serially increased concentrations of a salt sufficient to produce the high salinity tolerant microalgae strain, wherein the microalgae strain is a green algae, a red algae or a diatom and the subjecting step comprises growing the microalgae cell in a medium having an initial salinity in a range from about 0 ppt to about 45 ppt and increasing the salt concentration to a salinity in a range from about 50 ppt to about 400 ppt and wherein the serially increased concentrations of the salt comprise a series of salt additions to the medium that incrementally increase the salinity of the medium to two or more salinity levels, thereby exposing the microalgae cell to the serially increased salt concentrations to produce the high salinity tolerant microalgae strain; and recovering the high salinity tolerant microalgae cell, from the medium.

2. The method of claim 1, wherein the subjecting step comprises growing the microalgae cell at ambient air and/or ambient room temperature.

3. The method of claim 1, wherein the subjecting step comprises growing the microalgae cell using a natural and/or artificial light source.

4. The method of claim 1, wherein the series of salt additions comprises 2, 3, 4, 5, 6, 7, 8, 9 or 10 separate salt additions.

5. The method of claim 1, wherein the salinity is serially increased by about 5 ppt, 10 ppt, 20 ppt, 25 ppt, 30 ppt, 40 ppt, 50 ppt, or 75 ppt at each salt addition.

6. The method of claim 1, wherein the series of salt additions comprise two or more separate salt additions.

7. The method of claim 1, wherein the high salinity tolerant microalgae strain is produced in about 2 to about 14 days.

8. The method of claim 1, wherein the high salinity tolerant microalgae strain produces a secondary metabolite.

9. The method of claim 8, wherein the secondary metabolite is excreted by the high salinity tolerant microalgae strain.

* * * * *